United States Patent
Du et al.

(10) Patent No.: US 11,439,315 B2
(45) Date of Patent: Sep. 13, 2022

(54) MRI T1W AND T2W COMBINED FEATURES FOR DETECTING NEURODEGENERATION

(71) Applicant: The Penn State Research Foundation, University Park, PA (US)

(72) Inventors: Guangwei Du, Hershey, PA (US); Xuemei Huang, Hershey, PA (US); Mechelle Lewis, Hershey, PA (US)

(73) Assignee: The Penn State Research Foundation, University Park, PA (US)

( * ) Notice: Subject to any disclaimer, the term of this patent is extended or adjusted under 35 U.S.C. 154(b) by 185 days.

(21) Appl. No.: 16/970,029

(22) PCT Filed: Nov. 13, 2018

(86) PCT No.: PCT/US2018/060682
§ 371 (c)(1),
(2) Date: Aug. 14, 2020

(87) PCT Pub. No.: WO2019/172968
PCT Pub. Date: Sep. 12, 2019

(65) Prior Publication Data
US 2021/0106250 A1 Apr. 15, 2021

Related U.S. Application Data

(60) Provisional application No. 62/638,628, filed on Mar. 5, 2018.

(51) Int. Cl.
*A61B 5/055* (2006.01)
*A61B 5/00* (2006.01)
*G01R 33/56* (2006.01)

(52) U.S. Cl.
CPC ............ *A61B 5/055* (2013.01); *A61B 5/4082* (2013.01); *G01R 33/5601* (2013.01); *G01R 33/5602* (2013.01)

(58) Field of Classification Search
CPC ..... A61B 5/055; A61B 5/4064; A61B 5/4082; G01R 33/5601; G01R 33/5602
See application file for complete search history.

(56) References Cited

U.S. PATENT DOCUMENTS

| | | |
|---|---|---|
| 2008/0010166 A1 | 1/2008 | Yang et al. |
| 2011/0019908 A1 | 1/2011 | Wei |
| 2017/0039708 A1 | 2/2017 | Henry et al. |

OTHER PUBLICATIONS

International Preliminary Report on Patentability for PCT/US2018060682 dated Sep. 8, 2020.
Glasser MF et al, Mapping human cortical areas in vivo based on myelin content as revealed by T1- and T2-weighted MRI, J. Neurosci 2011; 11597-11616.
Righart R, et al. Cortical pathology in multiple sclerosis detected by the T1/T2-weighted ratio from routine magnetic resonance imaging, Ann. Neurol 2017; 82:519-529.

(Continued)

*Primary Examiner* — Mark D Remaly
(74) *Attorney, Agent, or Firm* — Buchanan Ingersoll & Rooney PC

(57) ABSTRACT

Embodiments can relate to a method for detecting a physiological condition by generating a Magnetic Resonance Image (MRI) contrast image comprising a T1 weighted (T1W) image/T2 weighted (T2W) ratio. Embodiments can further include using the T1W/T2W ratio to identify changes in substantia nigra pars compacta within a region of the brain.

20 Claims, 7 Drawing Sheets

(56) References Cited

OTHER PUBLICATIONS

International Search Report for PCT/US2018/060682 dated Jan. 11, 2019.
Written Opinion of the International Searching Authority for PCT/US2018/060682 dated Jan. 11, 2019.
Cosottini, M. et al., MR Imagining of the Substantia Nigra at 7 T Enables Diagnosis of Parkinson Disease. Radiology, Feb. 26, 2014; vol. 271, No. 3; pp. 831-838, p. 836, col. 2, paragraphs 1-2; p. 836, col. 3, paragraph 1; DOI: 10.1148/Radiol.14131448.
Yagi, S., et al., Progression from Unilateral to Bilateral Parkinsonism in Early Parkinson Disease: Implication of Mesocortical Dopamine Dysfunction by PET. Journal of Nuclear Medicine, Jul. 21, 2010; vol. 51, No. 8; pp. 1250-1257; figure 1; p. 1251, col. 1, paragraph 2; p. 1252, col. 2, p. 2; table 3; DOI: 10.2967/inumed.110.076802.
Fioravanti, V. et al., MRI Correlates of Parkinson's Disease Progression: A Voxel Based Morphometry Study. Parkinson's Disease, 2015; vol. 2015, No. 378032; pp. 1-9; table 1; p. 2, col. 1, paragraph 3; DOI: 10.1155/2015/378032.

MRI T1W AND T2W COMBINED FEATURES FOR DETECTING NEURODEGENERATION

CROSS-REFERENCE TO RELATED APPLICATIONS

This patent application is the U.S. national stage application of International Patent Application No. PCT/US2018/060682, filed on Nov. 13, 2018, which is related to and claims the benefit of priority to U.S. Provisional Application Ser. No. 62/638,628 filed on Mar. 5, 2018, the entire contents of which is incorporated herein by reference.

STATEMENT REGARDING FEDERALLY SPONSORED RESEARCH OR DEVELOPMENT

This invention was made with government support under Grant Nos. NS060722 and NS082151 awarded by the National institutes of Health. The Government has certain rights in the invention.

FIELD OF THE INVENTION

Embodiments can relate to a method for detecting a physiological condition by generating a Magnetic Resonance Image (MRI) contrast image comprising a T1 weighted (T1W) image/T2 weighted (T2W) ratio. Embodiments can further include using the T1W/T2W ratio to identify changes in substantia nigra pars compacta of the brain.

BACKGROUND OF THE INVENTION

Parkinson's disease (PD) can be linked to a loss of dopaminergic neurons in the substantia nigra pars compacta (SNc) of the basal ganglia. Conventional methods for identifying and monitoring changes in SNc and other biomarkers can utilize imaging techniques that lack standardized imaging procedures. In addition, conventional methods can be hindered by motion artifacts, yield inconsistent results, and be technically complex.

SUMMARY OF THE INVENTION

PD can be associated with dopamine neuron loss in the substantia nigra pars compacta (SNc). Embodiments of the methods disclosed herein can be used to identify changes in SNc, which can include a loss of dopamine neuron loss. Identifying a change in SNc can facilitate diagnosis of PD and/or monitoring stages or progression of PD. An embodiment of the method can involve generating a T1W image and a T2W image of an anatomical location of tissue. A T1W/T2W ratio can be generated for each anatomical location to produce a T1W/T2W ratio map.

In some embodiments, a first Magnetic Resonance Image (MRI) contrast image comprising a T1W/T2W ratio map can be generated for a specimen belonging to a cohort (a group of individuals having a physiological condition). The first MRI contrast image can be used as a MRI contrast image template for specimens of the cohort. Regions within the first MRI contrast image representative of changes in SNc can be identified. A second MRI contrast image of a second specimen can be generated. The second MRI contrast image can include a T1W/T2W ratio map. The second MRI contrast image can be compared to the MRI contrast image template. The comparison between the second MRI contrast image and the MRI contrast image template can be used to identify the second specimen as having the physiological condition associated with the cohort. The comparison can involve identifying differences between T1W/T2W ratio intensities of the second MRI contrast image and T1W/T2W ratio intensities of the MRI contrast image template.

In some embodiments, the physiological condition can be PD. Embodiments of the method can effectively identify changes in SNc even in specimens having the mildest form of PD (e.g., Hoehn Yahr stage I PD in the off medication state). Some embodiments of the method can involve gauging the physiological condition's severity. For example, embodiments of the method can involve distinguishing a change in SNc from a MRI contrast image taken of a first specimen that is in Hoehn Yahr stage I PD and a change in SNc from a MRI contrast image taken of a second specimen that is in Hoehn Yahr stage II PD.

In one embodiment, a method of identifying neurodegeneration can involve generating at least one first magnetic resonance image (MRI) contrast image of tissue of a first specimen belonging to a cohort. The at least one first MRI contrast image can have a first T1-weighted (T1W)/T2-weighted (T2W) ratio map. The first T1W/T2W ratio map can have a plurality of T1W/T2W ratios for a plurality of anatomical locations of the first specimen's tissue. The cohort can include a group of specimen's having a form of neurodegeneration. The method can involve designating the at least one first MRI contrast image as a MRI contrast image template for the cohort. The method can involve generating a second MRI contrast image of tissue of a second specimen not being part of the cohort but suspected of having the form of neurodegeneration. The second MRI contrast image can include a second T1W/T2W ratio map. The second T1W/T2W ratio map can have a plurality of T1W/T2W ratios for a plurality of anatomical locations of the second specimen's tissue. The method can involve defining a region within the MRI contrast image template having a predetermined neurodegeneration-related change of substantia nigra pars compacta (SNc) associated with the form of neurodegeneration and extracting a T1W/T2W ratio intensity from this region. The method can involve comparing a T1W/T2W ratio intensity from the second T1W/T2W ratio map to the extracted T1W/T2W ratio intensity to identify a change of SNc in the second specimen's tissue. The method can involve determining that the change of SNc in the second specimen's tissue is representative of the predetermined neurodegeneration-related change of SNc of the cohort.

In some embodiments, the at least one first MRI contrast image can include a plurality of first MRI contrast images. Each individual first MRI contrast image can be generated for each cohort of a plurality of cohorts.

In some embodiments, the form of neurodegeneration can be a form of Parkinson's Disease (PD). For such embodiments, the plurality of cohorts can include: a first cohort comprising specimens having no form of PD; a second cohort comprising specimens having Hoehn Yahr stage I PD; and/or a third cohort comprising specimens having Hoehn Yahr stage II PD.

In some embodiments, the at least one first MRI contrast image can include a plurality of T1W images and T2W images for a plurality of anatomical locations of the first specimen's tissue. A T1W image for an anatomical location can be co-registered with a T2W image for the same anatomical location. The first T1W/T2W ratio map can be generated by dividing each T1W image signal intensity by its co-registered T2W image signal intensity. The second MRI contrast image can include a plurality of T1W images and T2W images for a plurality of anatomical locations of the second specimen's tissue. A T1W image for an anatomical location can be co-registered with a T2W image for the same anatomical location. The second T1W/T2W ratio map can be generated by dividing each T1W image signal intensity by its co-registered T2W image signal intensity.

In some embodiments, the predetermined neurodegeneration-related change of SNc can include a loss of dopaminerigic neurons. In other embodiments, the predetermined neurodegeneration-related change of SNc can include other changes.

In some embodiments, the first specimen's tissue can include a midbrain region of the first specimen. The second specimen's tissue can include a midbrain region of the second specimen.

In some embodiments, the comparing step can involve voxel-based analysis. In other embodiments, the comparing step can involve a region-of-interest based analysis.

In some embodiments, the method can further involve normalizing the plurality of T1W images and T2W images of the at least one first MRI contrast image and normalizing the plurality of T1W images and T2W images of the second MRI contrast image.

In one embodiment, a method of identifying a physiological condition can involve generating a magnetic resonance image (MM) contrast image template of tissue of a first specimen belonging to a cohort. The Mill contrast image template can include a first T1-weighted (T1W)/T2-weighted (T2W) ratio map. The first T1W/T2W ratio map can include a plurality of T1W/T2W ratios for a plurality of anatomical locations of the first specimen's tissue. The method can involve generating a MRI contrast image of tissue of a second specimen not being part of the cohort but suspected of having a physiological condition associated with the cohort. The MRI contrast image can include a second T1W/T2W ratio map. The second T1W/T2W ratio map can include a plurality of T1W/T2W ratios for a plurality of anatomical locations of the second specimen's tissue. The method can involve comparing T1W/T2W ratio intensities of the first T1W/T2W ratio map to T1W/T2W ratio intensities of the second T1W/T2W ratio map to identify changes in substantia nigra pars compacta (SNc) in the second specimen's tissue.

In some embodiments, the physiological condition can be neurodegeneration (e.g. a form of Parkinson's Disease, etc.). In some embodiments, the changes in SNc can include a loss of dopaminerigic neurons. The loss of dopaminerigic neurons can be a loss that is at or exceeds a pre-selected threshold.

In some embodiments, the comparing step can involve neuroimaging. In other embodiments, the comparing step can involve at least one of voxel-based analysis and region-of-interest based analysis.

In some embodiments, the method can further involve co-registering the first T1W/T2W ratio map with the second T1W/T2W ratio map. The co-registering can involve aligning the MRI contrast image template with the MRI contrast image.

In some embodiments, the first specimen's tissue can include a midbrain region of the first specimen. The second specimen's tissue can include a midbrain region of the second specimen.

In one embodiment, a method of generating a magnetic resonance image (MRI) contrast image can involve generating, via a magnetic resonance scanner, a plurality of T1-weighted (T1W) images for a plurality of anatomical locations of tissue. The method can involve generating, via the magnetic resonance scanner, a plurality of T2-weighted (T2W) images for the plurality of anatomical locations of the tissue. The method can involve co-registering each T1W image of an anatomical location with each T2W image of the same anatomical location. The method can involve dividing each T1W image signal intensity by its corresponding co-registered T2W image signal intensity to generate a T1W/T2W ratio map of the tissue.

Some embodiments of the method can be implemented using a magnetic resonance imaging (MRI) scanner and at least one computer device connected to the scanner. The computer device can include hardware that includes a processor connected to a non-transitory computer readable medium. The medium may have a program and/or application stored thereon that can be run to have the computer device perform an embodiment of the method. A computer system that utilizes an MRI scanner and/or a computer that may have T1W images, T2W images, and MRI images stored in its non-transitory computer readable medium or stored in non-transitory computer readable medium that is connectable to the computer device (e.g. a remote server that has the images and/or other data stored in its non-transitory memory where the server is connectable to the computer device via at least one network having a plurality of nodes (e.g. access points, routers, servers, gateways, etc.). In some embodiments, a medical device system can include a computer device and an MRI scanner as well as other elements (e.g. a network that may facilitate a connection between the MRI scanner and the computer device or a network that may include a server that stores MRI scanner data (e.g. MRI images, etc.) generated by the MRI scanner that the computer device can access and utilize). It should be appreciated that embodiments of the computer device, non-transitory computer readable medium, and medical device system are also provided herein.

For example, a medical device apparatus can include a computer device having a processor connected to a non-transitory computer readable medium. The computer device can be configured to receive magnetic resonance image data generated by a magnetic resonance imaging scanner (MRI scanner). For example, the computer device can be communicatively connectable to the MRI scanner or to a server or other device that may receive MRI image data from the MRI scanner. The computer device can be configured to co-register each T1W image of the Mill image data for a patient with each T2W image of the same anatomical location of the patient and divide each T1W image signal intensity by its corresponding co-registered T2W image signal intensity to generate at least one T1W/T2W ratio map. The computer device can be configured to compare T1W/T2W ratio intensities of a first T1W/T2W ratio map to T1W/T2W ratio intensities of a second T1W/T2W ratio map of a pre-selected first cohort to identify changes in substantia nigra pars compacta (SNc) that are at or exceed a first pre-selected threshold value to detect a physiological condition of the patient. The computer device can also be configured to compare T1W/T2W ratio intensities of the first T1W/T2W ratio map to T1W/T2W ratio intensities of a third T1W/T2W ratio map of a pre-selected second cohort to identify changes in substantia nigra pars compacta (SNc) that are at or exceed a second pre-selected threshold value to detect a physiological condition of the patient. The computer device can also be configured to compare T1W/T2W ratio intensities of the first T1W/T2W ratio map to T1W/T2W ratio intensities of a fourth T1W/T2W ratio map of a pre-selected third cohort to identify changes in substantia nigra pars compacta (SNc)

that are at or exceed a third pre-selected threshold value to detect a physiological condition of the patient.

In some embodiments, the physiological condition that is to be detected can be a form of Parkinson's Disease (PD). The first, second, and third cohorts can be patients having PD, patients within Hoehn-Yahr stage I, and patients within Hoehn-Yahr stage II (e.g. the first cohort can be representative patients having PD, the second cohort can be representative patients having PD that are in Hoehn-Yahr stage I, and the third cohort can be representative patients having PD within Hoehn-Yahr stage II). The first, second, and third pre-selected threshold values can be similar values, the same values, or different values.

Further features, aspects, objects, advantages, and possible applications of the present invention will become apparent from a study of the exemplary embodiments and examples described below, in combination with the Figures, and the appended claims.

BRIEF DESCRIPTION OF THE DRAWINGS

The above and other objects, aspects, features, advantages and possible applications of the present innovation will be more apparent from the following more particular description thereof, presented in conjunction with the following drawings. Like reference numbers used in the drawings may identify like components.

DETAILED DESCRIPTION OF THE INVENTION

Figure 1:
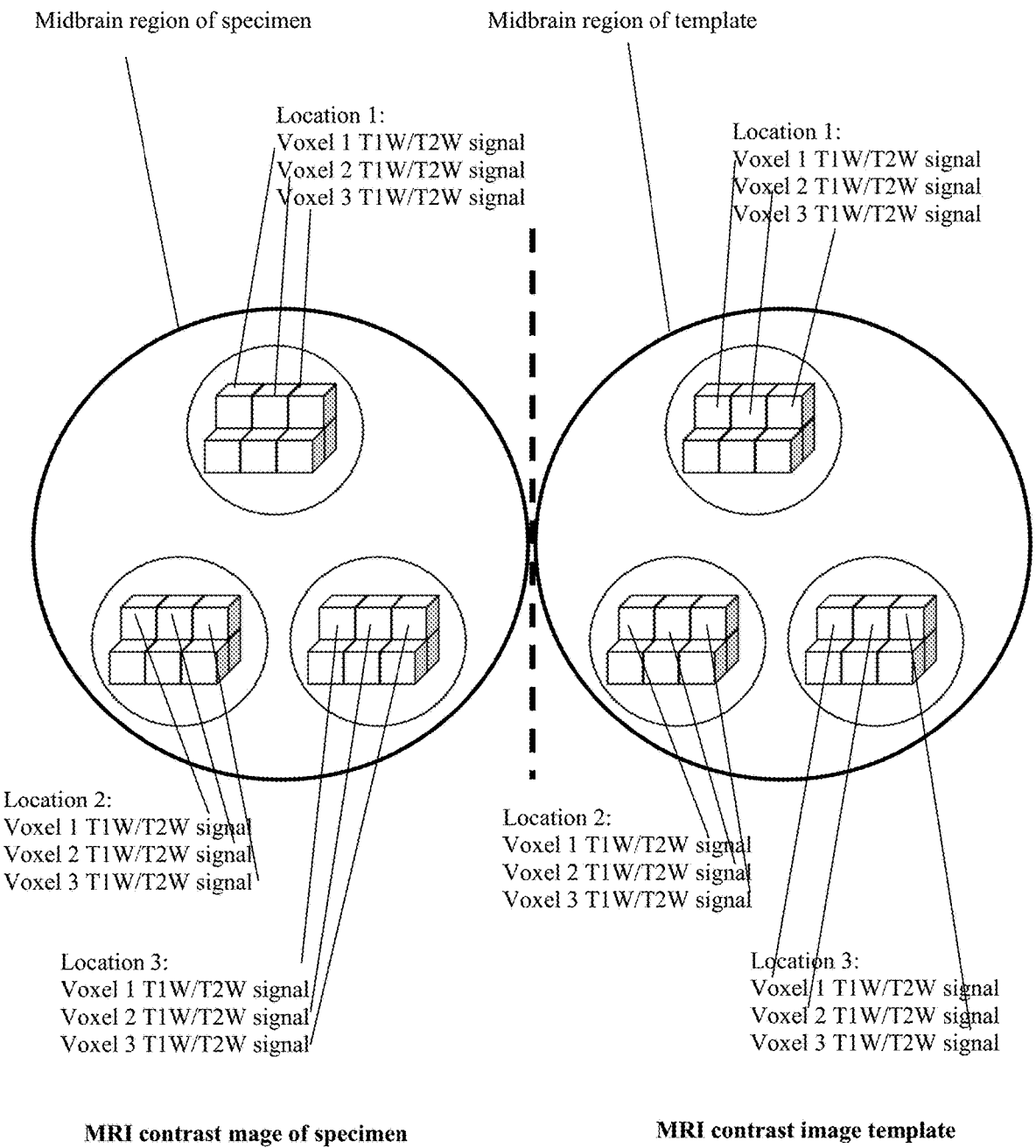
FIG. 1 shows an exemplary voxel co-registration technique that can be used with an embodiment of the method.

The following description is of exemplary embodiments that are presently contemplated for carrying out the present invention. This description is not to be taken in a limiting sense, but is made merely for the purpose of describing the general principles and features of the present invention. The scope of the present invention is not limited by this description.

Embodiments can include a method of identifying changes in SNc and an apparatus that can be used to implement the method (e.g. a computer device, a medical device system, etc.). In some embodiments, the change in SNc can include a loss of dopaminerigic neurons. With PD being linked to the loss of dopaminerigic neurons, identifying changes in SNc can facilitate detection of tissue (e.g., brain tissue) that has been affected by PD. For example, embodiments of the method can be used to study tissue of the subcortical structure of the midbrain region of a person suspected of suffering from PD. This can include using an MRI contrast image generated by an embodiment of the method as an in vivo marker for detecting PD-related changes in SNc. Using MRI contrast images generated by embodiments of method as an in vivo marker can facilitate diagnosing PD (even in the early stages of PD development), differentiating between stages of PD, and/or tracking the progression of PD related changes in SNc (i.e., tracking the progression of PD development). It is contemplated that embodiments can be used for assessing and tracking progression of other conditions in which a change in SNc can facilitate detection of a condition of a patient and tracking the evolution of that condition.

In some embodiments, the method can involve generating a MRI contrast image of tissue of a person (e.g. a patient). An MRI contrast image can be generated by scanning tissue of a person using a magnetic resonance imaging device (e.g. an MRI Scanner). An example of the magnetic resonance scanner can be a Trio (Siemens Magnetom, Erlangen, Germany), with an 8-channel phase array head coil. Of course, other magnetic resonance scanners can be used.

The MRI contrast image can include a T1W image and/or a T2W image. In some embodiments, the method can involve generating a Mill contrast image that is defined, at least in part, by a T1W/T2W ratio. In some embodiments, a MRI contrast image can be compared to a MRI contrast image template so that a quantitative contrast analysis can be performed to identify differences between T1W/T2W ratio intensities of the Mill contrast image and T1W/T2W ratio intensities of the MM contrast image template. This can be done to identify changes in SNc within the tissue of the person from which the MRI contrast image was taken.

Use of a Mill contrast image defined, at least in part, by a T1W/T2W ratio, can provide an image having high resolution (e.g., a high number of distinct pixels of an array of pixels that can be displayed), high reliability (e.g., a high rate of generating the same image for the same tissue), and/or high sensitivity (e.g., a high contrast in imagery for different tissue or for tissue exhibiting different characteristics). One of the reasons for this can be that generating a MRI contrast image defined, at least in part, by a T1W/T2W ratio can cancel MR-related intensity bias fields. Another reason can be that T1W and T2W images can have higher resolutions compared to other images. Another reason for this can be that the T1W/T2W ratio can depend on dendrite density but not myelin content of the tissue. Thus, a MRI contrast image defined, at least in part, by the T1W/T2W ratio that is representative of tissue of the midbrain can reflect a sum of multiple PD-related changes involving neurons, dendrites, microglia, and/or iron content.

A T1W image can be defined as spin-lattice relaxation time of a proton. In one embodiment, the method can involve subjecting tissue to an external magnetic field. This can involve subjecting the tissue to an external magnetic field via the MRI scanner. This can cause at least some of the spins of the protons of the tissue to be aligned. Being aligned can include the spins of the protons being in aligned precession with a longitudinal magnetization of the external magnetic field. The method can involve subjecting the tissue to at least one radiofrequency pulse. This can include applying the radiofrequency pulse to the tissue while the tissue is being subjected to the external magnetic field. This can include applying the radiofrequency pulse to the tissue during and/or after at least some of the spins of the protons within the tissue are aligned with the external magnetic field. The radiofrequency pulse can be generated by a radiofrequency pulse generator. In some embodiments, the radiofrequency pulse can be configured as a radio frequency waveform within the electromagnetic spectrum ranging from $1\times10^4$ Hertz to $3\times10^{11}$ Hertz. The radiofrequency pulse can cause at least some of the spins of the protons within the tissue to be mis-aligned with the longitudinal magnetization of the external magnetic field. The method can involve allowing at least some of the spins of the protons of the tissue to revert back to being aligned with the external magnetic field after the radiofrequency pulse is applied.

Not all of the spins of the protons of the tissue revert back to being aligned with the external magnetic field at a same rate. An amount of time at which a predetermined amount of spins of protons within the tissue revert to being aligned with the external magnetic field can be used to define a tissue magnetization vector. A T1W image can be an image that represents the longitudinal relaxation of the tissue's magnetization vector (e.g., the amount of time it takes a predetermined amount of spins of the protons to re-align with the longitudinal magnetization of the external magnetic field). With different tissue (e.g., fatty tissue v. non-fatty tissue), or the same tissue but with regions having different characteristics (e.g., a change in SNc), the relaxation times of the protons can vary. For example, protons of fat can realign more quickly than protons of water, and thus fatty tissue protons can realign more quickly than tissue having a larger water composition to it. The differences in the rates of re-alignment can be used to generate a contrast in imagery, and therefore provide an MRI image including a contrast that is representative of different tissue or representative of tissue having different characteristics. Embodiments of the method can involve generating a T1W image configured to illustrate differences in T1 relaxation of the spins of protons within the tissue.

A T2W image can be defined as spin-spin relaxation of the tissue magnetization vector. The spin-spin relaxation can be the amount of spins of the protons within the tissue that decay from being mis-aligned. For example, the radiofrequency pulse can cause at least some of the spins of the protons of the tissue to align (e.g., be in an aligned precession) in a direction that is transverse to the longitudinal magnetization of the external magnetic field. The spins of these protons can decay from this alignment after the radiofrequency pulse is applied. The amount of spins and the rates at which the spins of the protons decay can differ. The differences in the amount and rates of decay can be used to generate a contrast in imagery. Embodiments of the method can involve generating a T2W image configured to illustrate differences in T2 relaxation of the spins of the protons within the tissue.

Embodiments of the method can involve generating a MRI contrast image that includes a T1W image and a T2W image. Using image co-registration techniques and array system computing techniques, T1W images and T2W images of an anatomical location of the tissue can be co-registered. This can include matching a T1W image of a first anatomical location of the tissue with the T2W image of the first anatomical location of the tissue. Co-registration of T1W and T2W images can also be performed for other anatomical locations. For example, a T1W image of a second anatomical location of the tissue can be co-registered with a T2W image of a second anatomical location of the tissue, a T1W image of a third anatomical location of the tissue can be co-registered with a T2W image of the third anatomical location of the tissue, etc. A plurality of co-registered T1W and T2W images can be compiled to generate a MRI contrast image depicting the differences in T1 relaxation of the spins of protons within the tissue and the differences in T2 relaxation of the spins of protons within the tissue at each anatomical location simultaneously.

In some embodiments, the plurality of T1W and T2W images can be normalized. For example, a reference anatomical region (something other than the tissue suspected of having a change in SNc—a temporal muscle, orbital cavity fat tissue, etc.) can be used to provide a reference for intensity normalization. Normalizing the T1W and T2W images can be done to reduce variance that may be caused by magnetic field inhomogeneity. As another example, each of the specimens from which the MRI contrast image is taken can be aligned in space, allowing for a co-registration of each T1W image and T2W image of one MRI contrast image with each T1W image and T2W image of another MRI contrast image, the co-registration being to a common spatial coordinate system.

As noted herein, embodiments of the method can involve generating a MRI contrast image defined, at least in part, by a T1W/T2W ratio. A T1W/T2W ratio can be defined by a ratio of a T1W image to a T2W image. For example, a T1W image signal intensity generated for the first anatomical location of the tissue can be divided by a T2W image signal intensity generated for the first anatomical location of the tissue to generate a T1W/T2W ratio for the first anatomical location. A T1W/T2W ratio can be generated for more anatomical locations of the tissue. For example, a T1W image signal intensity generated for the second anatomical location of the tissue can be divided by a T2W image signal intensity generated for the second anatomical location of the tissue to generate a T1W/T2W ratio for the second anatomical location, a T1W image signal intensity generated for the third anatomical location of the tissue can be divided by a T2W image signal intensity generated for the third anatomical location of the tissue to generate a T1W/T2W ratio for the third anatomical location, etc. In some embodiments, a T1W/T2W ratio can be generated for a plurality of anatomical locations of the tissue. The plurality of T1W/T2W ratios for the plurality of anatomical locations of the tissue can be compiled to generate a T1W/T2W ratio map of the tissue. The T1W/T2W ratio map can be configured as a data structure that is storable in a computer readable medium. In some embodiments, the ratio map can be configured so that image signal intensity ratio values corresponding to different anatomical locations are identifiable via the map. In some embodiments, the T1W/T2W ratio map can be configured so that the map can be utilized to generate a display illustrating the different image signal intensity ratios at different anatomical locations in a graphical format or other format via a display connected to a computer device that may be configured to utilize the map to generate the display.

A T1W/T2W ratio map can be modified or revised so that a map is provideable for only a particular anatomical region of interest from an initial original anatomical location of the map (e.g. a map of a sub-region of the initial anatomical region of the initial map). A T1W/T2W ratio map can also, or alternatively, be filtered or otherwise adjusted to refine the map for subsequent use in other ways. In some embodiments, an image segmentation technique can be used to identify and segment regions within the T1W/T2W ratio map. For example, an atlas-based segmentation technique can be performed on the T1W/T2W ratio map. In some embodiments, utilization of such a technique can modify the map or can result in generation of a new map.

In some embodiments, the T1W/T2W ratio map can be rescaled based on a median T1W/T2W ratio of the T1W/T2W ratios comprising the T1W/T2W ratio map so as to allow T1W/T2W ratio values extracted from one MRI contrast image to be more comparable to T1W/T2W ratio values extracted from another MRI contrast image. In other embodiments, the T1W/T2W ratio map can be rescaled based on an average T1W/T2W ratio of at least some of the T1W/T2W ratios comprising the T1W/T2W ratio map so as to allow T1W/T2W ratio values extracted from one MRI contrast image to be more comparable to T1W/T2W ratio values extracted from another MRI contrast image. For example, a median average T1W/T2W ratio of the T1W/T2W ratios comprising the T1W/T2W ratio map can be used to rescale the T1W/T2W ratio map so as to allow T1W/T2W ratio values extracted from one MRI contrast image to be more comparable to T1W/T2W ratio values extracted from another MRI contrast image.

In some embodiments, the MR-related bias field can be removed from the T1W/T2W ratio map. For example, dividing T1W by T2W can reduce the MR-related bias field. In addition, or in the alternative, the MR-related bias field in the T1W image and/or the T2W image can be reduced via image processing techniques.

Some embodiments of the method involve generating a MRI contrast image of tissue within the midbrain of a specimen. The midbrain can be defined as a portion of the central nervous system associated with vision, hearing, motor control, sleep/wake, arousal (alertness), and temperature regulation. The midbrain can include the tectum, the tegmentum, the cerebral aqueduct, the cerebral peduncles, the crus cerebri, reticular formation and/or several nuclei and fasciculi. In some embodiments, the midbrain can be limited to only a sub-region of the tectum, the tegmentum, the cerebral aqueduct, the cerebral peduncles, the crus cerebri, reticular formation, and several nuclei and fasciculi. For instance, the midbrain region for the specimen that is used in an embodiment can only include the tectum and/or tegmentum in some embodiments. As another example, the midbrain region that is used may only utilize the tectum or may only utilize the superior and/or inferior colliculi of the tectum. As yet another example, the midbrain region that is used may only include the tegmentum or may only include the red nucleus, the periaqueductal gray, and/or the substantia nigra.

In some embodiments, an MRI contrast image of a specimen having predetermined physiological condition can be set as a MRI contrast image template. A MRI contrast image template can be generated for specimens belonging to a cohort. A cohort can be a group of specimens sharing a same or similar physiological condition. The physiological condition can be a stage of PD, for example.

Figure 2:
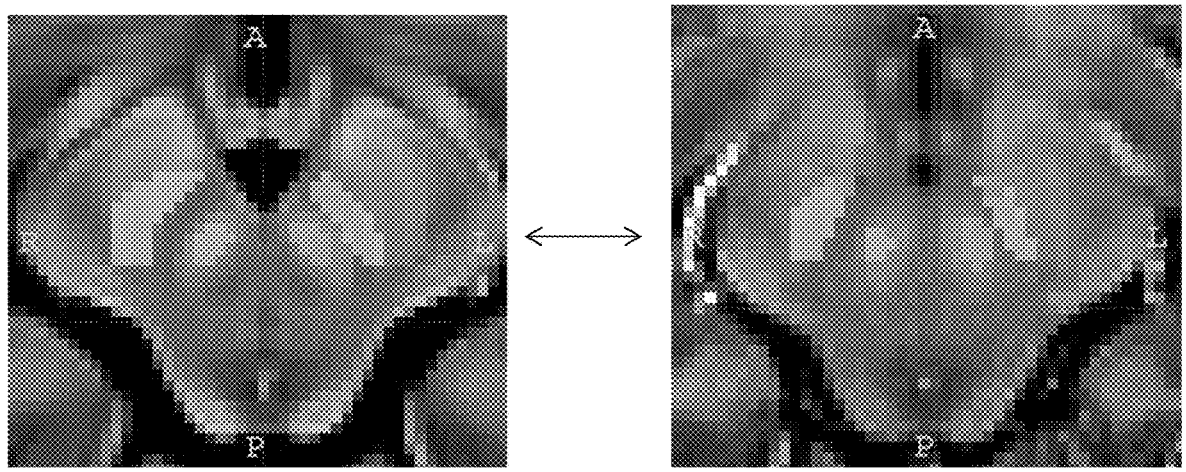
FIG. 2 shows a Mill contrast image co-registered with a Mill contrast image template.

Referring to FIGS. 1 and 2, some embodiments of the method can involve generating a MRI contrast image of tissue of a first specimen and comparing the Mill contrast image with a MRI contrast image template from a second specimen of a cohort in which it is suspected that the first specimen belongs. The second specimen may be suspected of having a condition shared by the first specimen but the second specimen is not part of the cohort of the first specimen. The comparison can include co-registering anatomical locations of the tissue from the Mill contrast image with anatomical locations of the tissue from the Mill contrast image template. The co-registration can include co-registering an anatomical location from the Mill contrast image with the same anatomical location from the Mill contrast image template. For instance an anatomical location of the midbrain region from the Mill contrast image can be co-registered with an anatomical location of the midbrain region from the Mill contrast image template. The anatomical location within the midbrain region associated with the MRI contrast image can be the same anatomical location within the midbrain region associated with the Mill contrast image template. Below are tables illustrating examples of co-registering of anatomical locations of tissue from an exemplary MRI contrast image with anatomical locations of the tissue from the MRI contrast image template.

Tables 1 and 2 are exemplary tables for a first cohort comparison with a patient's image data. The first cohort can include specimens having no form of PD, for example.

TABLE 1

Exemplary Table Illustrating Co-registration of Locations With Image Data of a First Cohort

| Corresponding Location | MRI contrast image template | Patient MRI contrast image |
|---|---|---|
| Midbrain Region 1 | (T1W image signal intensity at location 1)/(T2W image signal intensity at location 1) | (T1W image signal intensity at location 1)/(T2W image signal intensity at location 1) |
| Midbrain Region 2 | (T1W image signal intensity at location 2)/(T2W image signal intensity at location 2) | (T1W image signal intensity at location 2)/(T2W image signal intensity at location 2) |
| Midbrain Region 3 | (T1W image signal intensity at location 3)/(T2W image signal intensity at location 3) | (T1W image signal intensity at location 3)/(T2W image signal intensity at location 3) |

TABLE 2

Exemplary Table Illustrating Co-registration of Locations With Image Data of a First Cohort

| Corresponding Location | MRI contrast image template T1W | MRI contrast image template T2W | Patient MRI contrast image T1W | Patient MRI contrast image T2W |
|---|---|---|---|---|
| Midbrain Region 1 | T1W value at location 1 of midbrain region 1 | T2W value at location 1 of midbrain region 1 | T1W value at location 1 of midbrain region 1 | T2W value at location 1 of midbrain region 1 |
| Midbrain Region 2 | T1W value at location 1 of midbrain region 2 | T2W value at location 1 of midbrain region 2 | T1W value at location 1 of midbrain region 2 | T2W value at location 1 of midbrain region 2 |
| Midbrain Region 3 | T1W value at location 1 of midbrain region 3 | T2W value at location 1 of midbrain region 3 | T1W value at location 1 of midbrain region 3 | T2W value at location 1 of midbrain region 3 |

It should be appreciated that similar tables for second and third cohort template data can also be utilized for the patient's image data.

Tables 3 and 4 are exemplary tables for a second cohort comparison with a patient's image data. The second cohort can include specimens having Hoehn Yahr stage I PD, for example.

TABLE 3

Exemplary Table Illustrating Co-registration of Locations With Image Data of a Second Cohort

| Corresponding Location | MRI contrast image template | Patient MRI contrast image |
|---|---|---|
| Midbrain Region 1 | (T1W image signal intensity at location 1)/(T2W image signal intensity at location 1) | (T1W image signal intensity at location 1)/(T2W image signal intensity at location 1) |
| Midbrain Region 2 | (T1W image signal intensity at location 2)/(T2W image signal intensity at location 2) | (T1W image signal intensity at location 2)/(T2W image signal intensity at location 2) |
| Midbrain Region 3 | (T1W image signal intensity at location 3)/(T2W image signal intensity at location 3) | (T1W image signal intensity at location 3)/(T2W image signal intensity at location 3) |

TABLE 4

Exemplary Table Illustrating Co-registration of Locations With Image Data of a Second Cohort

| Corresponding Location | MRI contrast image template T1W | MRI contrast image template T2W | Patient MRI contrast image T1W | Patient MRI contrast image T2W |
|---|---|---|---|---|
| Midbrain Region 1 | T1W value at location 1 of midbrain region 1 | T2W value at location 1 of midbrain region 1 | T1W value at location 1 of midbrain region 1 | T2W value at location 1 of midbrain region 1 |
| Midbrain Region 2 | T1W value at location 1 of midbrain region 2 | T2W value at location 1 of midbrain region 2 | T1W value at location 1 of midbrain region 2 | T2W value at location 1 of midbrain region 2 |
| Midbrain Region 3 | T1W value at location 1 of midbrain region 3 | T2W value at location 1 of midbrain region 3 | T1W value at location 1 of midbrain region 3 | T2W value at location 1 of midbrain region 3 |

Tables 5 and 6 are exemplary tables for a third cohort comparison with a patient's image data. The third cohort can include specimens having Hoehn Yahr stage II PD, for example

TABLE 5

Exemplary Table Illustrating Co-registration of Locations With Image Data of a Third Cohort

| Corresponding Location | MRI contrast image template | Patient MRI contrast image |
|---|---|---|
| Midbrain Region 1 | (T1W image signal intensity at location 1)/(T2W image signal intensity at location 1) | (T1W image signal intensity at location 1)/(T2W image signal intensity at location 1) |
| Midbrain Region 2 | (T1W image signal intensity at location 2)/(T2W image signal intensity at location 2) | (T1W image signal intensity at location 2)/(T2W image signal intensity at location 2) |
| Midbrain Region 3 | (T1W image signal intensity at location 3)/(T2W image signal intensity at location 3) | (T1W image signal intensity at location 3)/(T2W image signal intensity at location 3) |

TABLE 6

Exemplary Table Illustrating Co-registration of Locations With Image Data of a Third Cohort

| Corresponding Location | MRI contrast image template T1W | MRI contrast image template T2W | Patient MRI contrast image T1W | Patient MRI contrast image T2W |
|---|---|---|---|---|
| Midbrain Region 1 | T1W value at location 1 of midbrain region 1 | T2W value at location 1 of midbrain region 1 | T1W value at location 1 of midbrain region 1 | T2W value at location 1 of midbrain region 1 |
| Midbrain Region 2 | T1W value at location 1 of midbrain region 2 | T2W value at location 1 of midbrain region 2 | T1W value at location 1 of midbrain region 2 | T2W value at location 1 of midbrain region 2 |
| Midbrain Region 3 | T1W value at location 1 of midbrain region 3 | T2W value at location 1 of midbrain region 3 | T1W value at location 1 of midbrain region 3 | T2W value at location 1 of midbrain region 3 |

Comparing a patient's MRI contrast image with MRI contrast image templates for the first cohort, the second cohort, and/or the third cohort can be done to determine if the patient has PD or, if the patient has PD, determine a stage of PD. For example, a comparison of patient's MRI contrast image with Mill contrast image template for the first cohort can be used to determine if the patient has no PD. A comparison of patient's MRI contrast image with MRI contrast image template for the second cohort can be used to determine if the patient has Hoehn Yahr stage I PD. A comparison of patient's MRI contrast image with Mill contrast image template for the second cohort can be used to determine if the patient has Hoehn Yahr stage II PD.

It should be appreciated that similar tables for a fourth, a fifth, a sixth, etc. cohort template data can also be utilized for the patient's image data. It should also be appreciated that a data structure can be generated to provide such a co-registering for subsequent use in embodiments of the method. Such a data structure may include a table similar to the exemplary tables provided above or may utilize some other mechanism of code or data to provide such co-registering.

FIG. 1 shows an exemplary voxel co-registration technique that can be used with an embodiment of the method. Voxels can be defined within anatomical locations of a region of tissue (e.g., a midbrain region). The voxels can be used to generate data structures representative of coordinates within the region of tissue. For example, each voxel can be provided with a value that is representative of its position relative to other voxels. The MRI contrast image of the midbrain region of the first specimen can be segmented into anatomical locations. For example, the MRI contrast image of the midbrain region of the first specimen can be segmented into a first anatomical location, a second anatomical location, and a third anatomical location, each anatomical location having a plurality of voxels. The MRI contrast image template of the midbrain region of the second specimen can be segmented into anatomical locations. For example, the MM contrast image template of the midbrain region of the second specimen can be segmented into a first anatomical location, a second anatomical location, and a third anatomical location, each anatomical location having a plurality of voxels. The data structures representing the coordinates of the voxels in the MM contrast image of the first specimen can be co-registered with the coordinates of the voxels in the MM contrast image template of the second specimen.

Each voxel can include data structures that are representative of T1W signals, T2W signals, and/or T1W/T2W signals. The T1W/T2W intensities of the T1W/T2W signals of the voxels of the MRI contrast image can be compared to the T1W/T2W intensities of the T1W/T2W signals of the co-registered voxels of the MM contrast image template. FIG. 2 shows a MRI contrast image co-registered with a MRI contrast image template. While the embodiment illustrated by FIG. 1 depicts T1W/T2W signals being used for co-registration, it should be noted that co-registration can be done with T2W signals only or with synthetic images (e.g., a combination of both T1W and T2W signals). For example, T1W signals can exhibit a good contrast on a gray and white matter boundary, whereas T2W signals can exhibit a good contrast to for showings subcortical nuclei (e.g., substantia nigra), which can be an important structure for Parkinson's disease. Thus, one skilled in the art will appreciate, with the benefit of the present disclosure, that any one or combination of T1W signals, T2W signals, synthetic images of T1W and T2W signals, and T1W/T2W signals can be used to meet desired design criteria for the co-registration.

In an exemplary implementation, during co-registration, a first image (e.g., a target image) is generated. The target image in this scenario can be the MRI contrast image template. A second image (e.g., a moving image) is also generated. The moving image in this scenario can be the MRI contrast image. Image registration can involve use of algorithms to spatially transform the MRI contrast image to align with the MRI contrast image template. This can involve keeping the reference frame in the MRI contrast image template stationary, while other datasets are transformed to match those of the MM contrast image. Matching can be done via intensity-based methods that compare intensity patterns in images via correlation metrics to determine a likeness or similarity in the images being compared. Matching can also be done via feature-based methods that find a correspondence between image features such as points, lines, and contours to determine a likeness or similarity in the images being compared. With any technique, the matching can involve an iterative process in which a similarity index is used at each iteration to determine how well the moving image matches with the target image. For instance, the similarity index can be used as a threshold value by which the likeness of the matched signals is evaluated.

It should be noted that other co-registration techniques can be used.

It should be understood that the above exemplary "image signal intensity" referenced in the above exemplary tables can be a value that is derived from a detected signal intensity at a particular location or can be a value that represents a detected signal intensity or a measured signal intensity. It should also be appreciated that each midbrain region (e.g. "Midbrain Region 1", etc.) identified in the above exemplary table can be different regions within a particular midbrain subpart (e.g. the tectum, the superior cooliculi, and/or inferior colliculi, the tegmentum, the red nucleus, the periaqueductal gray, and/or the substantia nigra) or different regions of the midbrain. The values used in the table or other data structure to identify the regions may be a value that is pre-selected to identify such a region. It should be understood that the above exemplary "image signal intensity" referenced in the above exemplary tables can be a value that is derived from a detected signal intensity at a particular location or can be a value that represents a detected signal intensity or a measured signal intensity. It should also be appreciated that each midbrain region (e.g. "Midbrain Region 1", etc.) identified in the above exemplary table can be different regions within a particular midbrain subpart (e.g. the tectum, the superior cooliculi, and/or inferior colliculi, the tegmentum, the red nucleus, the periaqueductal gray, and/or the substantia nigra) or different regions of the midbrain. The values used in the table or other data structure to identify the regions may be a value that is pre-selected to identify such a region.

With the benefit of the present disclosure, it can be inferred that T1W/T2W ratios are reflective of certain PD related neuron loss, sequential dendrite loss, microglial cell loss and inflammatory response, altered physical property of tissue, etc. Use of such ratios and comparison of ratios obtained from one or more images of a patient specimen with one or more images of a template for the same specimen (e.g. same midbrain region) can facilitate the detection of condition and/or monitoring of the progression of a patient condition.

Neuroimaging, such as voxel-based analysis, can be used to perform a voxel-based group comparison between the MRI contrast images of different pathophysiological condition groups. This can be done to identify tissue regions that have differences in T1W/T2W ratio intensities. These tissue regions can be designated as regions experiencing changes in SNc. For example, PD related neuron loss and sequential dendrite loss can alter the physical properties of the tissue, the altered physical properties being detected by the T1W/T2W ratio. It is contemplated that the T1W/T2W ratio can detect these altered physical properties because the ratio combines the detected changes detected by the T1W image and the T2W image.

In some embodiments, a region can be defined on a MRI contrast image template for specimens belonging to cohort having PD and known to have changes in SNc within that region. This region can be defined as a bilateral SNc region. A T1W/T2W ratio can be extracted from the bilateral SNc region. The extracted T1W/T2W ratio can be defined as a SNc T1W/T2W ratio. In some embodiments, the SNc T1W/T2W ratio can be used to perform a region-of-interest based analysis on MRI contrast images taken of specimens suspected of having PD. The region-of-interest based analysis can include identifying differences in SNc T1W/T2W ratio intensities of a MRI contrast image taken from a specimen suspected of having PD as compared to SNc T1W/T2W ratio intensities of a MRI contrast image template for a specimen belonging to a healthy control. For example, a SNc T1W/T2W ratio taken from a MRI contrast image template can be compared to a region-of-interest of a MRI contrast image of a specimen suspected of having a physiological condition that is indicative of the cohort from which the MRI contrast image template was generated. Generating Mill contrast image templates for various cohorts can allow a user to utilize the method to perform region-of-interest based analyses of Mill contrast images for specimens belonging to various groups. For example, embodiments of the method can be used to perform region-of-interest based analyses of MRI contrast images for specimens belonging to a control group, specimens belonging to a PD group, specimens belonging to a PD subgroup, etc. For instance, the region-of-interest based analysis can involve obtaining a SNc T1W/T2W value for each specimen belonging to a PD group, a PD subgroup, or a control group. A diagnosis of a specimen having a form of PD can be performed based on a group comparison. In addition, or in the alternative, a correlation can be done to identify clinical severity and monitor progression of the form of PD for that specimen diagnosed as having a form of PD. The correlation can be between the SNc T1W/T2W value (e.g., an imaging marker) and clinical measures (e.g., Unified Parkinson's Disease Rating Scale, Montreal Cognitive Assessment, etc.).

Figure 3:
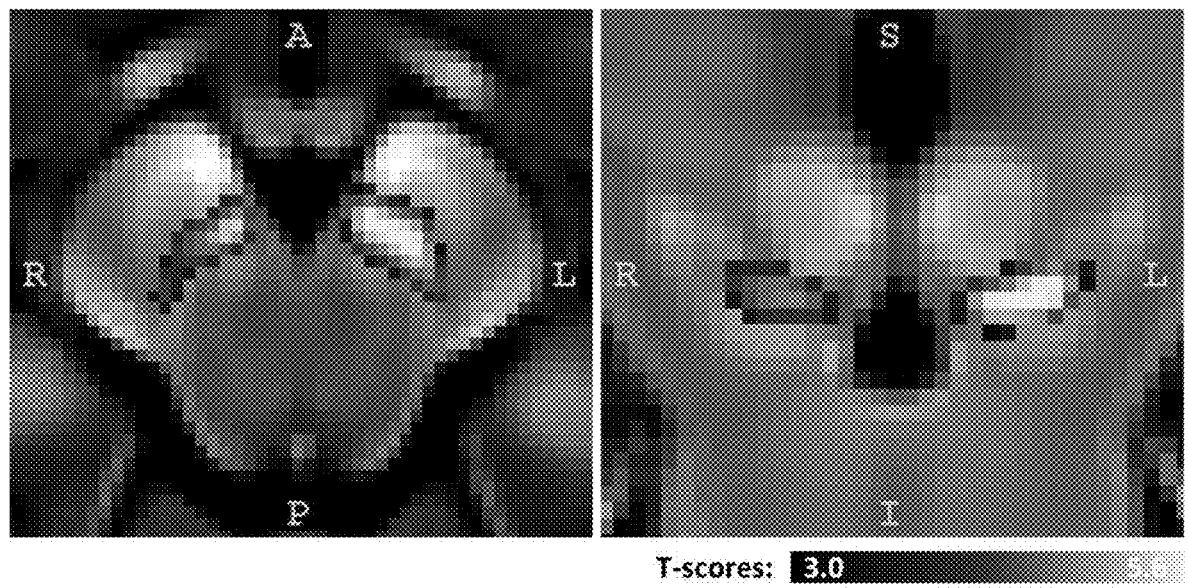
FIG. 3 shows a voxel-wise analysis of T1W/T2W ratio maps of the midbrain area of a specimen generated from an embodiment of the method, wherein an axial view of the midbrain area is shown in the left image and a coronal view of the midbrain area is shown in the right image.
Figure 4:
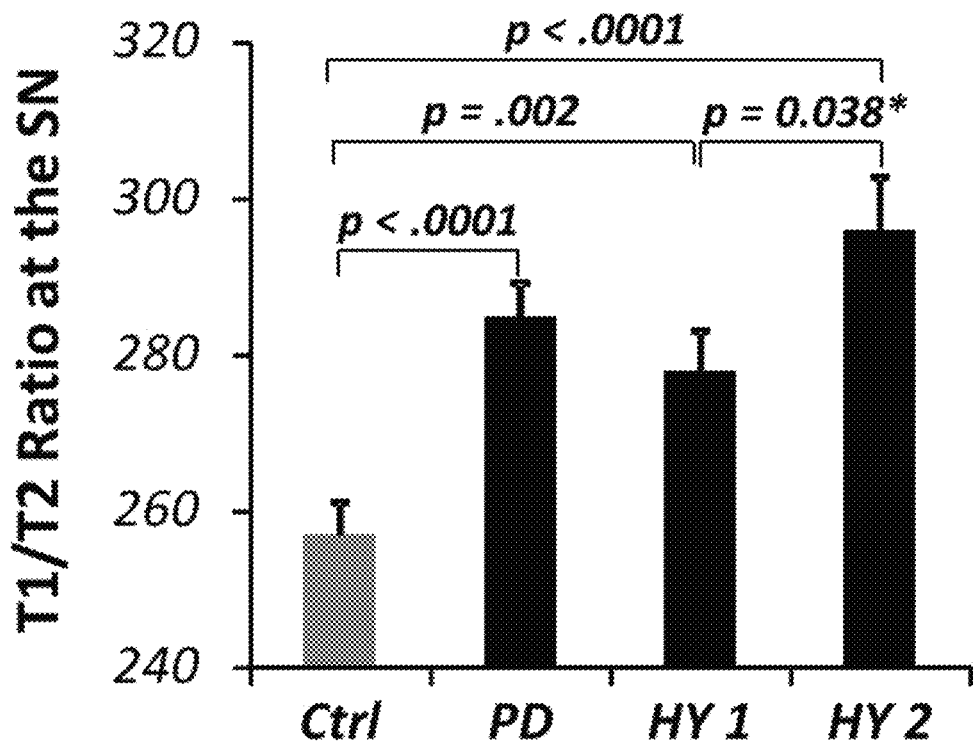
FIG. 4 shows a region of interest based analysis of T1W/T2W ratio maps of the midbrain area of specimen generated from an embodiment of the method.

FIG. 3 shows a voxel based analysis on tissue of the midbrain region of a specimen that may be generated using an embodiment of the method. The image on the left is an axial view of the midbrain region and the image on the right is a coronal view of the midbrain region. FIG. 3 shows changes between an MRI contrast image of a specimen having a form of PD and an MRI contrast image of a specimen in a healthy control group. The brighter in color areas indicate a change in T1W/T2W ratio intensities. The brighter the color (e.g. the more white the color), as indicated via the score bar included in FIG. 3, is indicative of a greater change in T1W/T2W ratio intensities in those areas. FIG. 4 shows an exemplary region-of-interest analysis results as a graphical display that may be generated using an embodiment of the method. Such a displayed graphical representation may be provided by a computer device via a display of that computer device (e.g. a liquid crystal display or monitor of the device). The graphical representation may be generated as defined by code of an application that is run by a processor of the computer device, for example.

The region-of-interest analysis results can pertain to specimens belonging to a control group (annotated as "Ctrl"), specimens belonging to a PD group (annotated as "PD"), specimens belonging to a PD Hoehn Yahr stage I subgroup (annotated as "HY 1"), and specimens belonging to a PD Hoehn Yahr stage II subgroup (annotated as "HY 2"). The p-values for comparisons between the groups are displayed on the graph of FIG. 3.

Figure 5:
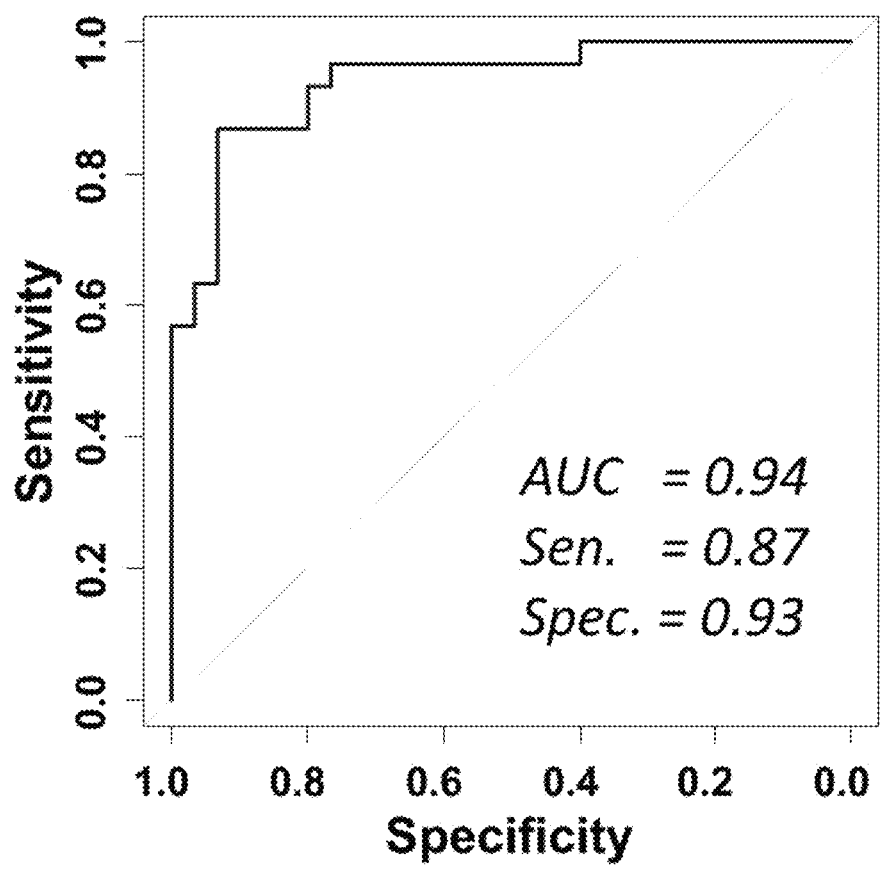
FIG. 5 shows a receiver operating characteristic curve analysis of T1w/T2w ratio maps of the midbrain area of specimen generated from an embodiment of the method.

FIG. 5 shows a receiver operating characteristic curve analysis demonstrating the sensitivity and the specificity that may be achieved with an embodiment of the method. The sensitivity and the specificity can be measures of how well MRI contrast images generated from an embodiment of the method can be used to differentiate between specimens belonging to a group or a subgroup. The receiver operating characteristic curve analysis can be achieved via a logistic regression of SNc T1W/T2W ratios plotted on a specificity v. sensitivity plot (PD statuses can be used as the dependent variable and SNc T1W/T2W values can be used as the independent variable). An area-under-the-curve (AUC) statistic of 0.94 (with a confidence interval of =0.88-1.0) can be achieved with an embodiment of the method. High sensitivity (Sen.) (0.87 or a 87% rate of probability of detection of specimens not within the control group) and high specificity (Spec.) (0.93 or a 93% rate of probability of detection of specimens within the control group) can also be achieved. This helps show that embodiments of the method can be used to analyze a patient's MRI imaging results with MRI template image materials to detect a patient having a particular PD condition and shows that such a detection can be reasonably made in a reliable manner. It is contemplated that embodiments of the method and apparatus can be configured to allow an early diagnosis of PD in patients and help provide care at an earlier intervention time period. It is contemplated that this can provide a means of allowing for an earlier diagnosis and earlier intervention, which may help better treat PD for a large number of patients as compared to convention treatment and diagnostic methodologies that are currently employed.

Figure 6:
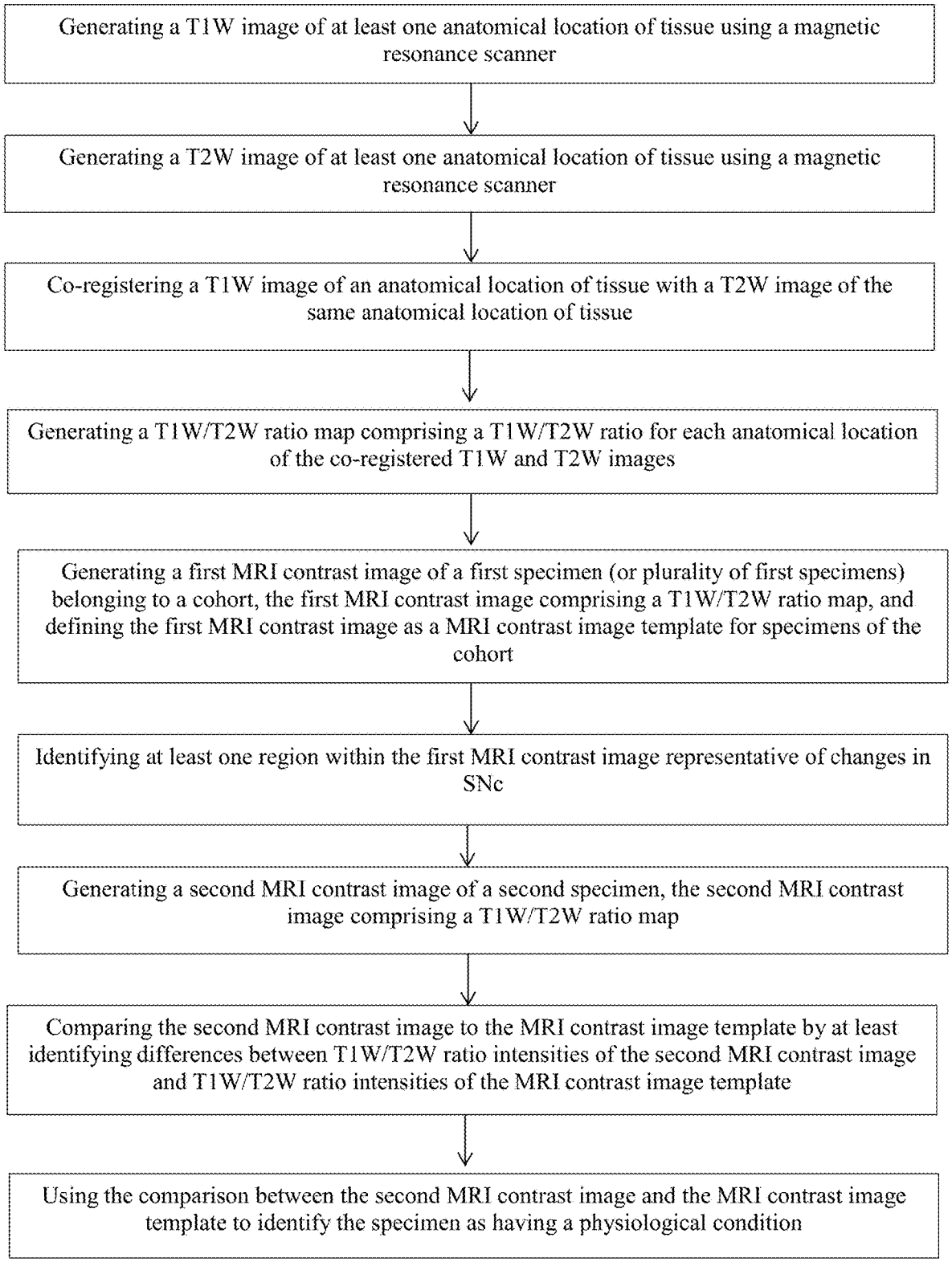
FIG. 6 shows an exemplary flow diagram that can be used for carrying out an embodiment of the method.

FIG. 6 shows an exemplary flow diagram illustrating steps that can be taken to carry out an embodiment of the method. Embodiments of the method can be used for detecting a physiological condition by generating a Mill contrast image comprising a T1W image/T2W ratio. The physiological condition can be a neurodegeneration, such as a change in SNc associated with PD, which can include a loss of dopaminergic neurons. The method can involve generating the Mill contrast image of tissue of a specimen. The specimen can be a human suspected of having the physiological condition. The tissue can be at least a portion of the midbrain region of the specimen.

Figure 7:
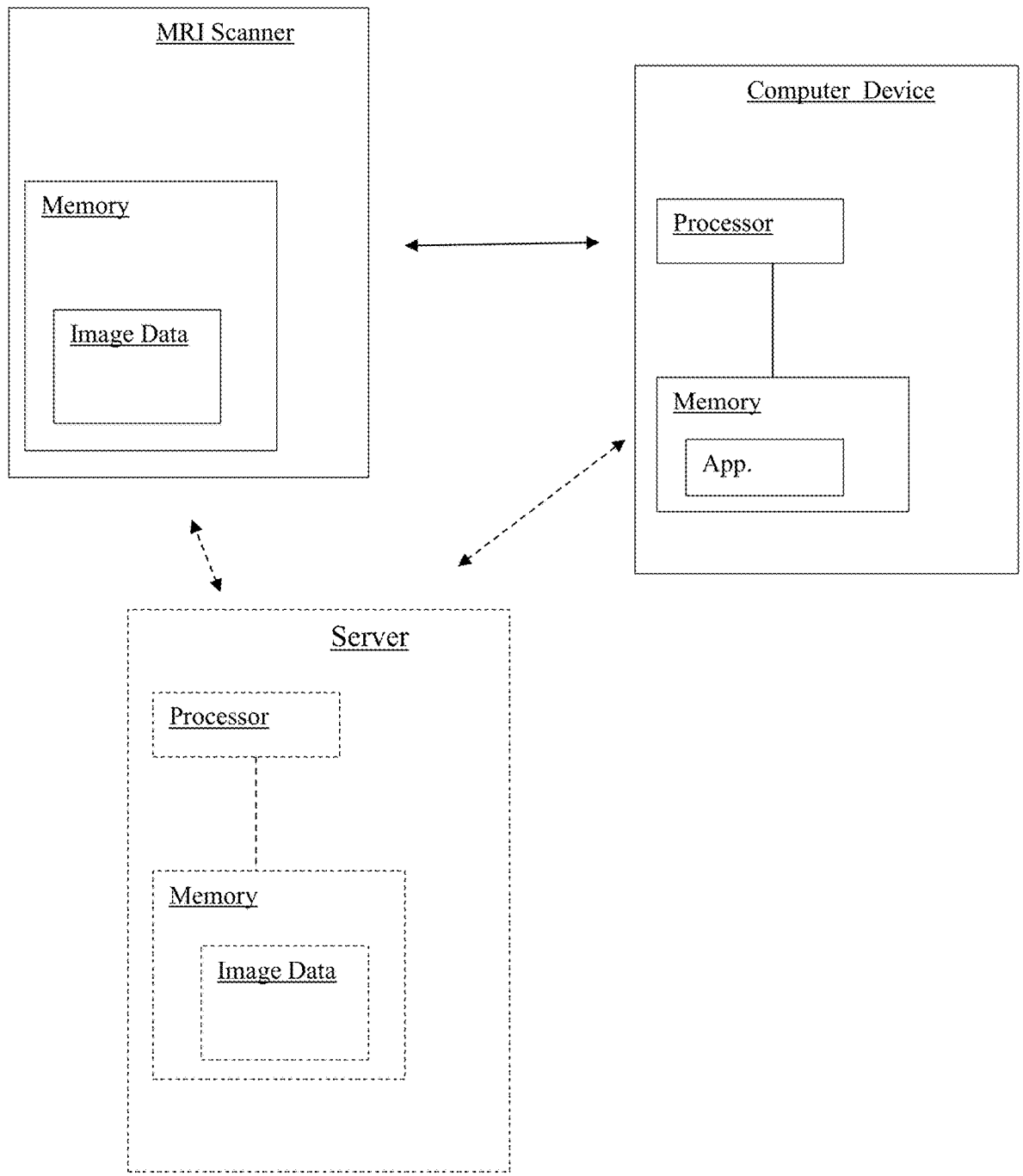
FIG. 7 shows an exemplary medical device apparatus that can be configured to implement an embodiment of the method.

Embodiments of the method can involve generating a T1W image of an anatomical location of the tissue using a magnetic resonance scanner, or MRI scanner. Some embodiments can involve generating a T2W image of an anatomical location of the tissue using a magnetic resonance scanner, or MM scanner. These images or image data of these images can be transmitted by the Mill scanner to a server for storage in the non-transitory memory of the server as shown in broken line in FIG. 7 (e.g. via a data connection provided via a network connection etc.). If stored in a server, a computer device running a program or application ("App.") may access the image data stored at the server (e.g. via a network connection or other communicative connection). Alternatively, the MRI scanner can transmit the image data to the computer device for storage in the non-transitory memory of the computer device for subsequent use by the computer when the App. is run by the processor of the computer device (e.g. via a direct wired communication connection, a direct wireless communication connection, or a network communication connection). The computer device may perform the method based on the image data received from the MRI scanner of the patient and MRI template image data. Such a methodology can employ the methodology disclosed herein and/or the exemplary methodology illustrated in FIG. 6.

Some embodiments can involve co-registering the T1W image of an anatomical location of tissue with the T2W image of the same anatomical location of tissue. In some embodiments, a plurality of co-registered T1W and T2W images for a plurality of anatomical locations can be compiled to generate a MRI contrast image that is representative of differences in T1 relaxation of the spins of protons within the tissue and the differences in T2 relaxation of the spins of protons within the tissue at each anatomical location.

Embodiments of the method can involve dividing the T1W image signal intensity by the co-registered T2W image signal intensity for a given anatomical location. This can generate a T1W/T2W ratio for the anatomical location. A T1W/T2W ratio can be generated for each anatomical location for which a T1W image and a T2W image is co-registered. This can facilitate compiling a plurality of T1W/T2W ratios to generate a T1W/T2W ratio map of the tissue.

Some embodiments can involve generating a first MRI contrast image of a first specimen belonging to a cohort. The first MRI contrast image can be generated for tissue of the midbrain region of the first specimen, for example. The cohort can be a group of humans known to have a physiological condition, such as a form of PD for example. The first MRI contrast image can include a first T1W/T2W ratio map of the tissue.

Some embodiments can involve generating the first MRI contrast image from a plurality of first specimens belonging to the cohort. For example, the first MRI contrast image can be an average image of a plurality of MRI images from a plurality of first specimens. The average image can be generated by layering each MRI image of each first specimen so that each point in the resultant MRI image is the mean average of values at that point in all of the MRI images. The first MRI contrast image can be generated for a target tissue of the first specimen(s) (e.g., the midbrain) or a region of the target tissue (e.g., the tectum, the tegmentum, the cerebral aqueduct, the cerebral peduncles, the crus cerebri, etc.). Thus, the first MRI contrast image can be an average image of midbrain tissue from a plurality of first specimens, or can be an average image of one or more regions of the midbrain tissue (e.g., the tectum, the tegmentum, etc.) from a plurality of first specimens.

The method can involve defining the first MRI contrast image as a MRI contrast image template for specimens of the cohort. Some embodiments can involve identifying at least one region within the first MRI contrast image representative of changes in SNc that is representative of the physiological condition of the specimen belonging to the cohort. The identified region(s) can be defined at a bilateral SNc region. The method can involve extracting at least one T1W/T2W ratio from the bilateral SNc region of the MRI contrast image template. The extracted T1W/T2W ratio(s) can be defined as SNc T1W/T2W ratio(s).

Some embodiments can involve generating a second MRI contrast image of a second specimen. The second MRI contrast image can be generated for tissue of the midbrain region of the second specimen. The second specimen can be a human suspected of having a physiological condition shared by the first specimen, but the second specimen is not part of the cohort. The second MRI contrast image can include a second T1W/T2W ratio map of the tissue.

The first T1W/T2W ratio map can be co-registered with the second T1W/T2W ratio map. This can include matching each anatomical location of the first T1W/T2W ratio map with a same anatomical location of the second T1W/T2W ratio map. This can be done to align the second MRI contrast image with the MRI contrast image template.

Some embodiments can involve comparing the second MRI contrast image with the MRI contrast image template. The method can involve using neuroimaging, such as voxel-based morphometry, to compare the he second MRI contrast image with the Mill contrast image template. A voxel-based analysis can be used to identify regions of the second MRI contrast image having T1W/T2W ratio intensities that differ from the T1W/T2W ratio intensities of the same regions of the Mill contrast image template. For example, a voxel-based analysis can be performed to provide a group comparison (e.g., comparing Mill contrast images of specimens within different groups and a healthy control group) at a voxel level. At each voxel, a t-test or an analysis of covariance (ANCOVA) can be used to test the difference between MRI contrast images of specimens within a PD group and MRI contrast images of specimens within a healthy control group.

In addition or in the alternative to a voxel-based analysis, the method can involve use of a region-of-interest analysis to compare the second MRI contrast image with the MRI contrast image template. This can involve comparing SNc T1W/T2W ratio intensities of a bilateral SNc region from the Mill contrast image template with T1W/T2W ratio intensities of a region within the second Mill contrast image corresponding to anatomical locations that co-register with the bilateral SNc region. For example, the region within the second MRI contrast image can be an area of interest. The method can involve comparing the T1W/T2W ratio intensities of a first area of interest to SNc T1W/T2W ratio intensities of a first bilateral SNc region of the MRI contrast image template corresponding to anatomical locations that co-register with the first area of interest. This can be done for additional areas of interest. For example, the method can involve comparing the T1W/T2W ratio intensities of a second area of interest to SNc T1W/T2W ratio intensities of a second bilateral SNc region of the MRI contrast image template corresponding to anatomical locations that co-register with the second area of interest. The method can involve comparing the T1W/T2W ratio intensities of a third area of interest to SNc T1W/T2W ratio intensities of a third bilateral SNc region of the MRI contrast image template corresponding to anatomical locations that co-register with the third area of interest.

Some embodiments can involve using the comparison between the second MRI contrast image and the MRI contrast image template to identify the specimen as having a physiological condition (e.g., Parkinson's Disease).

A non-limiting, exemplary implementation of the method was performed to assess the effectiveness of the method. MRI contrast images were used to study the substantia nigra of 30-early-stage (disease duration<2 years, Hoehn-Yahr stage I-II) PD patients and 30 age- and sex-matched control patients. Midbrain T1w/T2w ratio maps were analyzed using both voxel-based and region-of-interest approaches in normalized space. The sensitivity and specificity of the SNc T1W/T2W ratio was calculated using receiver-operating-characteristic (ROC) curve analysis to assess whether embodiments of the method could differentiate MRI contrast images of PD patients from MRI contrast images of control patients. T1W/T2W ratio maps of midbrain regions of specimens in early-stage PD patients and were matched with T1W/T2W ratio maps of midbrain regions of specimens of control patients and compared to develop a marker to assist in the early diagnosis of PD and gauge disease progression with high translational potential. The study included determining: 1) whether T1W/T2W ratio maps could capture PD nigral pathology; 2) whether a T1W/T2W ratio change detected in a PD-related T1W/T2W ratio map would be more severe in patients with a more advanced stage of the disease gauged by Hoehn-Yahr (HY) staging; and 3) whether the T1W/T2W ratio could be used to differentiate MRI contrast images of specimens of PD patients from MRI contrast images of specimen of control patients with high sensitivity and specificity.

Thirty early-stage PD patients (disease duration<2 years, 19 in HY stage I and 11 in HY stage II) and 30 age- and sex-matched controls were included from a large cohort. The participants were recruited from a tertiary movement disorders clinic (see Table 7 for detailed demographic information). Statistical analyses were performed using Student's t tests (for age), Fisher's exact test (for sex), and analysis of covariance with adjustments for age and sex (for HDRS, MoCA). UPDRS III: Unified Parkinson's Disease Rating Scale III motor subscore; LEDD: Levodopa equivalent daily dosage; HDRS: Hamilton Depression Rating Scale; MoCA: Montreal Cognitive Assessment.

TABLE 7

Demographic And Clinical Data For PD patients And Control Patients

|  | PD (n = 30) | Controls (n = 30) | P value |
| --- | --- | --- | --- |
| Age (years) | 60.5 ± 9.3 | 59.9 ± 8.2 | 0.77 |
| Female (%) | 15 (50%) | 15 (50%) | 1.00 |
| Disease duration (years) | 0.82 ± 0.58 | — | — |
| Hoehn-Yahr Stage (I/II) | 19/11 | — | — |
| UPDRS III | 16.5 ± 9.2 | — | — |
| LEDD | 293 ± 239 | — | — |
| HDRS | 7.0 ± 4.2 | 3.6 ± 2.3 | 0.0003 |
| MoCA | 25.4 ± 2.6 | 26.3 ± 2.3 | 0.11 |

PD diagnosis was confirmed by a movement disorder specialist according to United Kingdom brain bank criteria. Disease duration was defined as the date of PD diagnosis was first diagnosed by a physician. Unified Parkinson's Disease Rating Scale part III motor scores (UPDRS III) were obtained for each PD patient after withholding all PD medication overnight (~12 hours). Hoehn-Yahr staging was rated in the "off" medication state. Hamilton Depression Rating Scale (HDRS), Montreal Cognition Assessment (MoCA), and levodopa equivalent dosage (LEDD) also were obtained. All controls were free of any neurological, psychiatric, or major medical conditions.

All patients were scanned with a 3.0 Tesla MR scanner (Trio, Siemens Magnetom, Erlangen, Germany, with an 8-channel phase array head coil) with high resolution T1- and T2-weighted (T1W and T2W) images. A magnetization-prepared rapid acquisition gradient echo sequence was used to obtain T1W images with repetition time/echo time=1,540/2.34 ms, field of view=256×256, slice thickness=1 mm (with no gap), and slice number=176. A 3D T2W Sampling Perfection with Application Optimized Contrast using Different Angle Evolution (SPACE) sequence was used to obtain T2W images with repetition time/echo time=2,500/316 ms and the same spatial resolution settings as with T1W images. All T1W and T2W images were inspected offline and deemed free of severe motion artifacts or any major structural abnormalities.

T1W/T2W ratio maps for each patient then were generated. The T1W and T2W images were also processed to remove the bias field. The T2W image then was co-registered to the T1W image using a rigid registration to improve the alignment between the T1W and T2W images. An atlas-based segmentation approach was used to segment the reference region (fat-rich facial region) for intensity calibration. The raw T1W/T2W ratio maps were rescaled based on the median T1W/T2W ratio value in the reference region to yield final calibrated T1W/T2W ratio images for each patient.

A voxel-based analysis was performed on the midbrain region of the images to detect the exact location of the T1W/T2W ratio difference between PD patients and control patients. First, a cohort-specific T1W/T2W ratio template was created from all patients. Second, T1W/T2W ratio maps were co-registered to the T1W/T2W ratio template images. An FSL Randomise tool (Analysis Group, FMRIB, Oxford, UK) was used to conduct voxel-wise two-sample unpaired t-tests with age and sex as nuisance variables and the threshold-free cluster enhancement (TFCE) option to control for family-wise error. A p-value of 0.01 and cluster size of 100 was then used to define significant regions.

A bilateral SNc region was defined on the template image by defining 5 slices from superior to inferior, starting from one slice lower than the middle of the red nucleus. A kidney-shaped region ventrolateral to the red nucleus and dorsomedial to the SN pars reticulata (hypo-intensity band between the cerebral peduncles and red nucleus visualized in T2W images) was identified as the SNc region. The T1W/T2W ratio was extracted from each bilateral SNc region of a group and a subgroup for comparison and discriminative analysis. Demographic data of the patients were compared between groups and subgroups using the Chi-square exact test for sex and two-tailed Student's t-test for age. Clinical scores were compared using analysis of covariance with age and sex as covariates.

For the region-of-interest based approach, group comparisons of T1W/T2W ratio values from images taken were performed between control patients and PD patients and between HY stage I patents and HY stage II patients. The comparisons were conducted using analysis of covariance adjusted for age and sex. Statistical significance was defined as p<0.05. The ability of the method to use SNc T1w/T2w values for discriminating between MRI contrast images from specimens within PD stages and to discriminate between MRI contrast images from specimens of PD patient and control patients was assessed using logistic regression and receiver operating characteristic (ROC) curve analyses of the region-of-interest based T1W/T2W values. All statistical analyses were performed using R version 3.14.

MRI contrast images from PD patients displayed a significantly higher T1W/T2W ratio in the midbrain region. (See FIG. 3). The total region (cluster size) of significant T1W/T2W change was 320 mm$^3$, distributed in the right (126 mm$^3$, with a peak p-value=0.0002) and left (194 mm$^3$, with a peak p-value=0.00003) midbrain. The location of the significant area was ventrolateral to the red nucleus and dorsomedial to the SN pars reticulata (within the hypo-intensity band between the red nucleus and cerebral peduncle), which is a region consistent with the location of the SNc.

Compared to MRI contrast images of control patients, MRI contrast images of PD patients showed an increased T1W/T2W ratio value in the SNc region (e.g., 257±4.2 for control patients, 285±4.2 for PD patients, p<0.0001). (See FIG. 4). MRI contrast images of patients within Hoehn-Yahr stage I (n=19) and Hoehn-Yahr stage II (n=11) shows that both stage I and II groups had significantly higher T1W/T2W ratios (278±5.1 for stage I, p=0.002; and 296±6.8 for stage II, p<0.0001) compared to control patients. MRI contrast images of patients within the two PD subgroups indicated that the T1W/T2W ratio values were significantly higher for Hoehn-Yahr stage II patients than for Hoehn-Yahr stage I patients (p=0.039).

Using SNc T1W/T2W ratio values derived from the region-of-interest based approach, logistic regression analysis showed that the SNc T1W/T2W ratio can be a predictor for separating PD patients from control patients (p<0.0001). As seen in FIG. 5, the area-under-the-curve (AUC) statistic was 0.94 with a confidence interval of 0.88-1.0. In addition, high sensitivity (0.87) and specificity (0.93) using the Youden's index criteria was achieved. Compared to control patients, PD patients showed an increased T1W/T2W ratio in both the right (cluster size=129 mm$^3$, p=0.0002) and left (cluster size=194 mm$^3$, p=0.00003) midbrain that was located ventrolateral to the red nucleus, which corresponded to the SNc. The region-of-interest approach confirmed the group differences in the SNc.

It should be understood that modifications to the embodiments disclosed herein can be made to meet a particular set of design criteria. For instance, the number of or configuration of magnetic resonance scanners, MRI contrast images, MRI contrast image templates, radiofrequency pulse generators, and/or other components or parameters may be used to meet a particular objective.

It will be apparent to those skilled in the art that numerous modifications and variations of the described examples and embodiments are possible in light of the above teachings of the disclosure. The disclosed examples and embodiments are presented for purposes of illustration only. Other alternative embodiments may include some or all of the features of the various embodiments disclosed herein. For instance, it is contemplated that a particular feature described, either individually or as part of an embodiment, can be combined with other individually described features, or parts of other embodiments. The elements and acts of the various embodiments described herein can therefore be combined to provide further embodiments.

Therefore, it is the intent to cover all such modifications and alternative embodiments as may come within the true scope of this invention, which is to be given the full breadth thereof. Additionally, the disclosure of a range of values is a disclosure of every numerical value within that range, including the end points. Thus, while certain exemplary embodiments of apparatuses and methods of making and using the same have been discussed and illustrated herein, it is to be distinctly understood that the invention is not limited thereto but may be otherwise variously embodied and practiced within the scope of the following claims.

We claim:

1. A method of identifying neurodegeneration, comprising:
   generating at least one first magnetic resonance image (MRI) contrast image of tissue of a first specimen belonging to a cohort, the at least one first MRI contrast image comprising a first T1-weighted (T1W)/T2-weighted (T2W) ratio map, the first T1W/T2W ratio map comprising a plurality of T1W/T2W ratios for a plurality of anatomical locations of the first specimen's tissue, the cohort comprising a group of specimen's having a form of neurodegeneration;
   designating the at least one first Mill contrast image as a Mill contrast image template for the cohort;
   generating a second Mill contrast image of tissue of a second specimen not being part of the cohort but suspected of having the form of neurodegeneration, the second MRI contrast image comprising a second T1W/T2W ratio map, the second T1W/T2W ratio map comprising a plurality of T1W/T2W ratios for a plurality of anatomical locations of the second specimen's tissue;
   defining a region within the Mill contrast image template having predetermined neurodegeneration-related change of substantia nigra pars compacta (SNc) associated with the form of neurodegeneration and extracting a T1W/T2W ratio intensity from the region;
   comparing a T1W/T2W ratio intensity from the second T1W/T2W ratio map to the extracted T1W/T2W ratio intensity to identify a change of SNc in the second specimen's tissue; and
   determining that the change of SNc in the second specimen's tissue is representative of the predetermined neurodegeneration-related change of SNc of the cohort.

2. The method recited in claim 1, wherein the at least one first MRI contrast image comprises a plurality of first Mill contrast images, wherein an individual first Mill contrast image is generated for each cohort of a plurality of cohorts.

3. The method recited in claim 2, wherein the form of neurodegeneration is a form of Parkinson's Disease (PD).

4. The method recited in claim 3, wherein:
   the plurality of cohorts comprises:
      a first cohort comprising specimens having no form of PD;
      a second cohort comprising specimens having Hoehn Yahr stage I PD; and
      a third cohort comprising specimens having Hoehn Yahr stage II PD.

5. The method recited in claim 1, wherein:
   the at least one first MRI contrast image comprises a plurality of T1W images and T2W images for a plurality of anatomical locations of the first specimen's tissue, wherein a T1W image for an anatomical location is co-registered with a T2W image for the same anatomical location, and the first T1W/T2W ratio map is generated by dividing each T1W image signal intensity by its co-registered T2W image signal intensity; and
   the second Mill contrast image comprises a plurality of T1W images and T2W images for a plurality of anatomical locations of the second specimen's tissue, wherein a T1W image for an anatomical location is co-registered with a T2W image for the same anatomical location, and the second T1W/T2W ratio map is generated by dividing each T1W image signal intensity by its co-registered T2W image signal intensity.

6. The method recited in claim 1, wherein the predetermined neurodegeneration-related change of SNc identifies a loss of dopaminerigic neurons.

7. The method recited in claim 1, wherein:
   the first specimen's tissue comprises a midbrain region of the first specimen; and
   the second specimen's tissue comprises a midbrain region of the second specimen.

8. The method recited in claim 1, wherein the comparing step comprises voxel-based analysis.

9. The method recited in claim 1, wherein the comparing step comprises region-of-interest based analysis.

10. The method recited in claim 5, further comprising normalizing the plurality of T1W images and T2W images of the at least one first MRI contrast image and normalizing the plurality of T1W images and T2W images of the second MRI contrast image.

11. A method of identifying a physiological condition, comprising:
   generating a magnetic resonance image (MRI) contrast image template of tissue of a first specimen belonging to a cohort, the Mill contrast image template comprising a first T1-weighted (T1W)/T2-weighted (T2W) ratio map, the first T1W/T2W ratio map comprising a plurality of T1W/T2W ratios for a plurality of anatomical locations of the first specimen's tissue;
   generating a Mill contrast image of tissue of a second specimen not being part of the cohort but suspected of having a physiological condition associated with the cohort, the Mill contrast image comprising a second T1W/T2W ratio map, the second T1W/T2W ratio map comprising a plurality of T1W/T2W ratios for a plurality of anatomical locations of the second specimen's tissue; and
   comparing T1W/T2W ratio intensities of the first T1W/T2W ratio map to T1W/T2W ratio intensities of the second T1W/T2W ratio map to identify changes in substantia nigra pars compacta (SNc) in the second specimen's tissue as compared to the first specimen's tissue that are at or exceed a pre-selected threshold value to detect the physiological condition.

12. The method recited in claim 11, wherein the physiological condition comprises neurodegeneration.

13. The method recited in claim 12, wherein the neurodegeneration is a form of Parkinson's Disease (PD).

14. The method recited in claim 11, wherein the changes in SNc identifies a loss of dopaminerigic neurons.

15. The method recited in claim 11, wherein the generating of the MRI contrast image of the tissue of the second specimen comprises scanning the second specimen with an Mill scanner.

16. The method recited in claim 11, wherein the comparing step comprises at least one of voxel-based analysis and region-of-interest based analysis.

17. A medical device apparatus comprising:
a computer device having a processor connected to a non-transitory computer readable medium, the computer device configured to receive magnetic resonance image data generated by a magnetic resonance imaging scanner;
the computer device configured to co-register each T1W image of the magnetic resonance image data for a patient with each T2W image of the same anatomical location of the patient and divide each T1W image signal intensity by its corresponding co-registered T2W image signal intensity to generate at least one T1W/T2W ratio map; and
the computer device configured to compare T1W/T2W ratio intensities of a first T1W/T2W ratio map to T1W/T2W ratio intensities of a second T1W/T2W ratio map of a pre-selected first cohort to identify changes in substantia nigra pars compacta (SNc) that are at or exceed a first pre-selected threshold value to detect a physiological condition of the patient.

18. The medical device apparatus of claim 17, wherein the physiological condition is a form of Parkinson's Disease (PD).

19. The medical device apparatus of claim 18, wherein the computer device is also configured to compare T1W/T2W ratio intensities of the first T1W/T2W ratio map to T1W/T2W ratio intensities of a third T1W/T2W ratio map of a pre-selected second cohort to identify changes in substantia nigra pars compacta (SNc) that are at or exceed a second pre-selected threshold value to detect a physiological condition of the patient.

20. The medical device apparatus of claim 19, wherein the computer device is also configured to compare T1W/T2W ratio intensities of the first T1W/T2W ratio map to T1W/T2W ratio intensities of a fourth T1W/T2W ratio map of a pre-selected third cohort to identify changes in substantia nigra pars compacta (SNc) that are at or exceed a third pre-selected threshold value to detect a physiological condition of the patient; and wherein the medical device apparatus also includes the Mill scanner.

* * * * *